United States Patent

Honerlagen et al.

[11] Patent Number: 5,176,913
[45] Date of Patent: Jan. 5, 1993

[54] PROCESS FOR PREPARING A PARTIAL EXTRACT CONTAINING THE VOLATILE IN STEAM COMPONENTS AND FURTHER LIPOPHILIC COMPONENTS OF MEDICAL PLANTS AND/OR SPICE PLANTS

[75] Inventors: Hans J. Honerlagen, Unterägeri; Rudolf Steiner, Bassersdorf, both of Switzerland

[73] Assignee: Emil Flachsmann AG, Zurich, Switzerland

[21] Appl. No.: 371,387

[22] Filed: Jun. 23, 1989

[30] Foreign Application Priority Data

Jun. 24, 1988 [CH] Switzerland .......................... 2441/88

[51] Int. Cl.⁵ .............................................. A61K 35/78
[52] U.S. Cl. .................................. 424/195.1; 514/783; 426/386
[58] Field of Search ........................ 55/38; 424/195.1; 514/783; 426/386

[56] References Cited

U.S. PATENT DOCUMENTS

| | | | |
|---|---|---|---|
| 3,867,396 | 2/1975 | Dawes | 260/308 R |
| 4,370,151 | 1/1983 | Herbrechtsmeier et al. | 55/38 |
| 4,377,395 | 3/1983 | Herbrechtsmeier et al. | 55/38 |
| 4,704,161 | 11/1987 | White | 71/106 |

OTHER PUBLICATIONS

King, J. American Dispensatory 8th Ed. Cincinnati, 1870 pp. 970, 984.
Encyclopedia of Chemical Technology 1980 vol. 9 pp. 734–735, 116–118, 122–123.
Chem. Abstracts 1982 96:164551p Dehydration of Ethyl Formate, Bala.
Chem. Abstracts 1984 100:52526d Catalytic Production of Petroleum Resins, Benitez.
Chem. Abstracts 1985 Drying Organic Solvent 102:8928d Nippon Soda Co.
Chem. Abstracts 1986 105:227519m Lactam Purification, Moosavian.

Primary Examiner—Ronald W. Griffin
Assistant Examiner—Ralph Gitomer
Attorney, Agent, or Firm—Burns, Doane, Swecker & Mathis

[57] ABSTRACT

A partial extract containing the volatile in steam components and further lipophilic components of medical plants and/or spice plants or parts thereof, which may be charged in fresh or dried state, is obtained by a) mixing said plants or parts thereof with at least one organic solvent and extracting in usual manner, then either b) 1) adding to this extraction mixture at least one drying agent, in order to take away the water from the organic phase, and then separating the dried organic phase from the vegetable solid matter and from the drying agent, or b) 2) separating the vegetable solid matter from the organic phase, then adding to this organic phase at least one drying agent, in order to take away the water, and then separating the dried organic phase from the drying agent, and c) distilling the organic solvent(s), and recovering in this way a lipophilic concentrate.

17 Claims, No Drawings

PROCESS FOR PREPARING A PARTIAL EXTRACT CONTAINING THE VOLATILE IN STEAM COMPONENTS AND FURTHER LIPOPHILIC COMPONENTS OF MEDICAL PLANTS AND/OR SPICE PLANTS

FIELD OF THE INVENTION

The present invention is directed to a process for preparing a partial extract containing the volatile in steam components and further lipophilic components of medical plants and/or spice plants or parts thereof, which may be charged in fresh or dried state.

The invention is also directed to a process for preparing a complete extract containing the volatile in steam and further lipophilic components as well as the hydrophilic components from medical plants and/or spice plants or parts thereof, which may be charged in fresh or dried states.

DESCRIPTION OF THE PRIOR ART

Usually plant extracts are prepared by extraction with alcohols, mixtures of alcohols and water or just with water. In some few exceptions chlorinated hydrocarbons or low boiling hydrocarbons are used, such as e.g. in the hop-extraction for the brewing industry.

But in all cases only certain component groups are extracted, so that one is not able to speak of complete extracts, which contain the complete component spectra of the used plant.

It is also known that fresh Plants develop already enzymatic activities during the reduction to small pieces and thus, before they may be extracted, lose either completely or partially their native components. As an example the fresh garlic (Bulbus Alii sativi) is mentioned here. Up to now it was not possible to prepare a garlic extract, containing the alliin in an unchanged form. For this, see Miething H., Thober H., Apotheker Journal 10, pages 42–48 (1985) and Koch H. P., Deutsche Apotheker Zeitung 127, 8, pages 367–369 (1987). The allicin, which is valid since about 40 years as the active principle of the garlic, is formed immediately of the genuine precursor, the alliin, during reduction to small pieces of the drug by the influence of the enzyme alliinase; see Koch H. P., Deutsche Apotheker Zeitung 127, 8, pages 367–369 (1987). In one clove of garlic, neither cut nor crushed, these two substances are present in separate cells; during the destruction of the cell walls both substances react immediately with each other. See Block E., Spektrum der Wissenschaft (May 1985) pages 66–72.

SUMMARY OF THE INVENTION

It is an object of the present invention to provide concentrates of partial extracts and complete extracts of medical plants and/or spice plants containing also the components volatile in steam. There shall be provided also extracts which are stable and contain the native components. These objects shall be realized with a simple, cheap and economical process.

Now it was found quite surprisingly that by extraction with at least one organic solvent, e.g. with lower alcohols and ketones, the components, volatile in steam, of medical plants and spice plants or parts thereof may be extracted and may be obtained in the native state, when during the extraction one takes away the water, introduced by the plant, from the solvent or when one dehydrates the extract, also named menstruum, before the evaporation.

It was also found quite surprisingly, that plants or parts thereof, which develop enzymatic activities already during reduction to small pieces and thus, before they may be extracted, have already lost completely or partially their native components, may not develop their enzymatic activities when a reduction to small pieces is carried out in at least one organic solvent, e.g. in lower alcohols or in ketones, and thus allow the production of extracts which are stable and contain the native components. The provision therefore is that either the amount of the solvent is chosen such that the water introduced by the plant, also named drug, is so small that no enzymatic activity is possible, or that the water in the extraction agent is removed immediately.

More specifically, in one aspect of the invention there is provided a process for preparing a partial extract of medical plants and/or spice plants, or parts thereof, which may be charged in a fresh or dried state, containing both the volatile-in-steam lipophilic components and the non-volatile-in-steam lipophilic components thereof. The process comprises (i) mixing a plant (or parts thereof) with at least one organic solvent and extracting to form an extraction mixture of an organic phase comprising volatile-in-steam lipophilic components and other lipophilic components of the plant, and a vegetable solid matter phase; (ii) adding a drying agent to remove water from the organic phase; (iii) separating a dried organic phase from the drying agent; and (iv) distilling the dried organic phase and recovering a lipophilic concentrate.

In another aspect of the invention there is provided a process for preparing a complete extract of medical plants and/or spice plants (or parts thereof) containing the hydrophilic components thereof and both volatile-in-steam lipophilic components and nonvolatile-in-steam lipophilic thereof. The process comprises obtaining a lipophilic concentrate in the manner described above; mixing the resulting vegetable solid matter residue with water or a water miscible diluted organic solvent and extracting to form a solid matter/liquid phase extraction mixture; separating the solid matter from the liquid phase; distilling the liquid phase to form a hydrophilic component concentrate; and mixing the hydrophilic and lipophilic concentrates to form a complete extract.

In one embodiment of preparing the lipophilic concentrate, the vegetable solid matter phase is separated from the organic phase prior to adding the drying agent. In another embodiment the drying agent is added to the extraction mixture containing both the organic phase and the vegetable solid matter phase, and then the dried organic phase is separated from the drying agent and the vegetable solid matter phase.

In preparing the lipophilic concentrate the dried organic phase contains not more than 2% by weight water. Preferably, the dried organic phase is essentially free of water.

In preparing the lipophilic concentrate distillation is preferably under vacuum at a temperature of up to 60° C. The lipophilic concentrate can comprise a pharmaceutically active substance, a resin, a smell and flavor providing substance, or a volatile-in-steam component. Such a volatile-in-steam components can be an etheral oil, a naphthoquinone derivative, or an alkaloid.

The drying agent can be added to the organic solvent prior to mixing the organic solvent with the plant or parts thereof. Also, the drying agent can be added to the mixture of the organic solvent and a plant or parts thereof during extraction.

The drying agent is preferably a vegetable-or animal- or chemical-water-adsorbing material. Suitable drying agents include tragacanth, gelatin, a water-free sodium sulfate, a water-free magnesium sulfate, a water-free calcium chloride, a molecular sieve, or combinations thereof.

In a preferred embodiment the organic solvent is a polar solvent such as an alcohol, especially a $C_1$ to $C_4$-alcohol, particularly ethanol or methanol, a ketone, especially a $C_3$ to $C_5$- ketone, particularly acetone, or an ester, especially an alkylacetate where the alkyl residue has preferably from 1 to 4 carbon atoms.

In a preferred aspect of the invention the plant or parts thereof is reduced to small pieces while in contact with the organic solvent.

According to the invention, the partial and complete extracts can be applied as a remedy or a spice.

DESCRIPTION OF THE PREFERRED EMBODIMENTS

In the inventive process the water in the organic phase may also be separated by means of membrane technology instead of the use of a drying agent.

When cloves of garlic are reduced to small pieces in an organic solvent, then the reaction between the alliin and the enzyme alliinase is tied off.

With the inventive process especially the following plants are extracted:
Acorrus calamus L. (Rhizom)
Allium - species (e.g.: A. cepa L., A. ursinum L., A. sativum L.; Bulbus)
Alpinia officinarum Hanoe (Rhizom)
Anethum graveolens L. (Fructus)
Angelica archangelica L. various different subspecies. (Rhizoma) Anthennis nobilis L. (Chamomilla romana. Herba)
Apium graveolens L. (Fructus)
Archum major Gaertn. (Radix)
Arnica montana L. (Flos)
Artemisia absinthium L. (Herba)
Artemisia dracuncuius L. (Herba)
Brassica nigra [L.]Koch (Semen)
Carum carvi L. (Fructus)
Chrysanthemum vulgare Asch. (Herba)
Cinnamomum camphora, various different species (Cortex)
Cinnamomum ceylanicum Nees. (Cortex)
Citrus: various different species (Folium, Flavedo, Fruct.)
Copaifera reticulata Duke (Balsam)
Coriandrum sativum L. (Fructus)
Cuminum cyminum L. (Fructus)
Curcuma zedoaria [Bergius] Roxb, and further sub species (Rhizoma)
Cusparia officinalis [Willd,]Eng. (Cortex)
Dipterocarpus turbinatus Gaertn, (Balsamum)
Drosera - species (D. rotundifolia L., D. ramentac xea Burch; Herba)
Elettaria cardamomum [L.] White et Mathon (Fructus)
Eucalyptus globulus Labill, (Folium)
Foeniculum vulgare Miller (Fructus)
Gaultheria procumbens L, (Folium)
Hedoma pulegioides [L.] Pers. (Herba)
Hibiscus abelmoshus L. (Semen)
Humulus lupulus L. [F]os, Glandulae)
Hysopus officinalis L. (Herba)
Illicium verum Hook.f. (Fructus)
Inuls helenium L. (Rhizoma)
Iris pallidà Lam. (Rhizoma)
Jasminum grandiflorum L. (Flos)
Laurus nobilis L. (Folium, (Fructus)
Lavendula officinalis, various different species (Flos)
Lawsonia inermis L. (Folium)
Levisticum offioinale Koch (Radix)
Matricaria chamomilla L. (Flos)
Melaleuca: various different varieties (Folium)
Melilotus officinalis [L.] Lam. em. Thuill. (Herba)
Melissa offioinalis L. (Herba)
Mentha, all varieties (Folium)
Myristica fragrans Houttuyn (Arillus, Semen)
Myrtus communis L. (Folium)
Ocimum basilicum L. (Herba)
Ocotea sassafras (Cortex)
Oenanthe aquatica [L.] Poir (Fructus)
Olibanum (Resinum) Origanum majorana L. and further sub species (Herba)
Petroselinum crispum [Mill.] Nym. (Fructus, Herba)
Pimenta dioica [L.] Merill (Fructus)
Pimpinella anisum L. (Semen)
Piper angustifolium Ruiz. et Pavon, (Folium)
Pogostemon patchouli Pell, (Folium)
Prunus laurocerasus L. (Folium)
Rosmarinus officinalis L. and further sub species (Folium)
Ruta graveolens L. (Herba)
Salvia officinalis L. and further sub species (Folium)
Santalum album L. (Lignum)
Sarothamnus scoparius [L.] Wimmer (Herba)
Sassafras albidum.[Nutt.] Nees (Lignum)
Satureja hortensis L. (Herba)
Syzyguim aromaticum Merr. et Perry (Flores, Folium)
Thymus scrpyllum L. (Herba)
Thymus vulgaris L. (Herba)
Tilia cordat Mill. and platyphyllos Scop. (Flos)
Valeriana officinalis and further sub species (Radix)
Zingiberia officinale Roscoe (Rhizoma)
  Plants with ethereal oils, such as e.g.
  Fructus anisi stellati
  Fructus anisi vulg.
  Fructus carvi
  Flores humuli lup.
  Fructus coriandri
  Fructus juniperi
  Fructus foeniculi
  Flores chamomillae
  Herba thymi
  Radix valerianae offic.
  Rhiz. zingiberis,
are fully extracted with lower alcohols or ketones according to known extraction processes; the menstruum is dehydrated before evaporation. The concentration of the dehydrated menstruum is preferably carried out in vacuum up to the total removal of the solvent. Obtained are the lipophilic components of the plant, including the ethereal oils. For example in the case of camomile the matricin is obtained, the precursor of the not very stable azulene.

The so extracted plants are then extracted either with cold or hot water or with water miscible diluted organic solvents.

This extract contains then all polar components of the plant. The menstruum is also evaporated under reduced pressure up to a sirup consistency and then dried according to known processes.

By combining both phases, preferably in the final formulation, complete extracts are obtained, which complete extracts have the activity spectrum of the medical plant or of the spice plant.

Plants without ethereal oils but having substances volatile in steam, such as e.g.

Herba droserae
Folia henna
Herba spartii scopar.
Herba meliloti offic.

are also extracted with lower alcohols or lower ketones, the menstruum is dehydrated before evaporation, so that the components volatile in steam remain completely in the evaporization concentrate. The drugs set free from their components, volatile in steam, are extracted then with water.

After a separate drying of both phases both phases are combined to a complete extract.

Suitable means for the dehydration of the organic phases are water-free sodium sulfate, gelatin or tragacanth.

When the residues are extracted with water, it is clear that the previously introduced drying agent may not be water soluble. In this case e.g. tragacanth, molecular sieves etc. are used.

The partial extracts or complete extracts, prepared according to this invention, preferably in the form of a lipophilic concentrate, or in the form of a concentrate containing the lipophilic and hydrophilic components, may be used in dependency of the respective extracted plant as a remedy or as a spice.

The following examples shall illustrate the invention.

EXAMPLE 1

10 kg ground valerian roots (Radix valerianae offic. l.) were wetted with 5 liters of 96% ethanol and let stand overnight. The next morning the wet drug was introduced into a percolation tube and then percolated with 75 liters of 96% ethanol at room temperature. The percolate was dehydrated by the addition of 3 kg gelatine powder and separated from the water containing gelatine by filtration. From the filtrate the solvent was removed at a maximum temperature of 40° C. and under reduced pressure. Obtained were 0.34 kg with an ethereal oil content of 5.3% by weight. The drug extracted with ethanol was dried in the air and then extracted with 80 liters hot water having a temperature of about 90° C. in a stirring process during 60 minutes. Then this was filtrated, and the filtrate was concentrated under reduced pressure at a maximum of 70° C. up to sirup consistency. The sirupy extract was dried then in a vacuum drying cabinet at a maximum of 70° C. There were obtained 1.25 kg dried extract.

For dispensing hard gelatine capsules were chosen. In each capsule 68 mg of the with ethanol obtained phase and 249.5 mg of the water phase were added, so that in each capsule the extraction compounds of 2.0 g valerian roots are contained.

The "Deutsche Monographie der Kommission E" (German Monograph of the Commission E) prescribes for valerian roots a single dose of extract from 2 to 3 g drug.

By the intake of one capsule the single dose is reached.

EXAMPLE 2

10 kg hop flower (Flores humuli lupuli) were extracted as described in Example 1.

Obtained were 1.6 kg solvent free ethanol phase having an ethereal oil content of 2.3% by weight.

Obtained were also 1.5 kg of dried water phase.

Also here hard gelatine capsules were prepared.

160 mg of the phase, obtained with ethanol, and 150 mg of the phase, obtained with water, were placed in each capsule.

The "Deutsche Standardzulassung" (German Standard Admission) for hop flower prescribe a single dose of 1 to 2 teaspoons of the fruit of the hop for the preparation of one cup of tea. One teaspoon hop flower weighs 1 g, so that the described capsule corresponds to a single dose.

EXAMPLE 3

30 kg fresh cloves of garlic were placed in 400 kg methanol.

The reduction to small pieces of the cloves of garlic was realized slowly and carefully in methanol by means of a cutting device. After the reduction to small pieces of all cloves of garlic extraction thereof for one hour at room temperature under stirring was carried out.

Then this was filtered, to the filtrate 16 kg water-free sodium sulfate were added and stirred for two hours. After 2 hours filtration was carried out, and the water-free filtrate was concentrated under reduced pressure at a maximum temperature of 40° C. to sirup consistency. The sirupy extract was then dried at a maximum temperature of 70° C. in a vacuum drying cabinet. Obtained were 1 kg dried extract containing about 8 % by weight of alliin. The with methanol extracted drug was dried in the air and then extracted with 240 liters of water during 1 hour at 90° C. After the separation of the drug residue the aqueous menstruum was concentrated at a maximum temperature of 70° C. under reduced temperature up to sirup consistency and then dried in the vacuum drying cabinet. Obtained were 5 kg of dried extract.

By mixing of 1 part of the with methanol obtained phase with 5 parts of the with water obtained phase a complete extract of garlic roots was obtained.

By this process a fivefold concentration of the fresh cloves of garlic is obtained.

When from the therapeutical view only the alliin containing phase is of value, then here a thirty-fold concentration of the fresh cloves of garlic is obtained.

By mixing with dried garlic powder a stable standardized remedy in the form of tablets, dragees or capsules may be prepared.

The dried drug powder may also be replaced by the addition of alliinase.

EXAMPLE 4

1 kg Herba spartii scop. (broom), roughly ground, were wetted with 500 ml of 96% ethanol and let stand overnight.

The next morning the wet drug was filled in into a percolation tube and then percolated with 7.5 liters of 96% ethanol at room temperature. The percolate was dehydrated by the addition of 0.3 kg gelatine powder and then separated by filtration of the water containing gelatine. The filtrate was separated at a maximum temperature of 40° C and a reduced pressure from the solvent. There were obtained 30 g with 24 % by weight of sparteine. The with ethanol extracted drug was extracted with 8 liters of hot water having a temperature of 90° C. in a stirring process and then further treated as described in Example 1. 110 g dried extract were obtained.

While there are shown and described present preferred embodiments of the invention, it is to be distinctly understood that the invention is not limited thereto, but may be otherwise variously embodied and practiced within the scope of the following claims.

We claim:

1. A process for preparing a partial extract of at least one of medical plants and spice plants, or parts thereof, containing both volatile-in-steam lipophilic components and non-volatile-in-steam lipophilic components thereof, said process comprising (i) mixing a plant or parts thereof with at least one organic solvent and extracting to form an extraction mixture of an organic phase containing volatile-in-steam lipophilic components and other lipophilic components of the plant, and a vegetable solid matter phase; (ii) adding a drying agent to remove water from the organic phase; (iii) separating a dried organic phase from the drying agent; and (iv) distilling the organic phase and recovering a lipophilic concentrate containing both volatile-in-steam lipophilic components and non-volatile-in-steam lipophilic components of the plant or parts thereof.

2. The process according to claim 1 characterized in that the plants to be extracted are selected from Acorus calamus L. (Rhizom)
Allium - species (A. cepa L., A. ursinum L., A. Sativum L.: Bulbus)
Alpinia officinarum Hance (Rhizom)
Anethum graveolens L. (Fructus)
Angelica archangelica L., various sub species (Rhizoma)
Anthemis nobilis L. (Chamomilla romana, Herba)
Apium graveolens L. (Fructus)
Arctium major Gaertn. (Radix)
Arnica montana L. (Flos)
Artemisia absinthium L. (Herba)
Artemisia dracunculus L. (Herba)
Brassica nigra [L.] Koch (Semen)
Carum carvi L. (Fructus)
Chrysanthemum vulgare Asch. (Herba)
Cinnamomum camphora, various species (Cortex)
Cinnamomum ceylanicum Nees. (Cortex)
Citrus (Folium, Flavedo, Fruct.)
Copaifera reticulata Duke (Balsam)
Coriandrum sativum L. (Fructus)
Cuminum cyminum L. (Fructus)
Curcuma zeodoaria [Bergius] Roxb. and sub species (Rhizoma)
Cusparia officinalis [Willd.] Eng. (Cortex)
Dipterocarpus turbinatus Gaertn. (Balsamum)
Drosera - species (D. rotundifolia L., D. ramentacea Burch;Herba)
Elettaria cardamomum [L.] White et Mathon (Fructus)
Eucalytpus globulus Labill, (Folium)
Foeniculum vulgare Miller (Fructus)
Gaultheria procumbens L. (Folium)
Hedoma pulegioides [L.] Pers. (Herba)
Hibiscus abelmoschus L. (Semen)
Humulus lupulus L. (Flos, Glandulae)
Hysopus officinalis L. (Herba)
Illicium verum Hook.f. (Fructus)
Inula helenium L. (Rhizoma)
Iris pallida Lam. (Rhizoma)
Jasminum grandiflorum L. (Flos)
Laurus nobilis L. (Folium, Fructus)
Lavendula officinalis, sub species (Flos)
Lawsonia inermis L. (Folium)
Levisticum officinale Koch (Radix)
Matricaria chamomilla L. (Flos)
Melaleuca: sub species (Folium)
Melilotus officinalis [L.] Lam. em. Thuill. (Herba)
Melissa officinalis L. (Herba)
Mentha, all species (Folium)
Myristica fragrans Houttuyn (Arillus, Semen)
Myrtus communis L. (Folium)
Ocimum basilicum L. (Herba)
Ocotea sassafras (Cortex)
Oenanthe aquatica [L.] Poir (Fructus)
Olibanum (Resinum)
Origanum majorana L. and sub species (Herba)
Petroselinum crispum [Mill.] Nym. (Fructus, Herba)
Pimenta dioica [L.] Merill (Fructus)
Pimpinella anisum L. (Semen)
Piper angustifolium Ruiz. et Pavon. (Folium)
Pogostemon patchouli Pell. (Folium)
Prunus laurocerasus L. (Folium)
Rosmarinus officinalis L. and sub species (Folium)
Ruta graveolens L. (Herba)
Salvia officinalis L. and sub species (Folium)
Santalum album L. (Lignum)
Sarothamnus scoparius [L.] Wimmer (Herba)
Sassafras albidum [Nutt.] Nees (Lignum)
Satureja hortensis L. (Herba)
Syzygium aromaticum Merr. et Perry (Flores, Folium)
Thymus serpyllum L. (Herba)
Thymus vulgaris L. (Herba)
Tilia cordata T. Mill. and platyphyllos Scop. (Flos
Valeriana officinalis and sub species (Radix)
Zingiberis officinale Roscoe (Rhizoma).

3. A process according to claim 1, wherein prior to adding the drying agent, the vegetable solid matter phase is separated from the organic phase.

4. A process according to claim 1, wherein the drying agent is added to the extraction mixture containing both the organic phase and the vegetable solid matter phase, and then the dried organic phase is separated from the drying agent and the vegetable solid matter phase.

5. A process according to claim 1, where in step (i) a plant or parts thereof is reduced to small pieces while in contact with the organic solvent.

6. A process according to claim 1, wherein the drying agent is added to the organic solvent prior to mixing the organic solvent with the plant or parts thereof.

7. A process according to claim 1, wherein the drying agent is added to the mixture of the organic solvent and a plant or parts thereof during extraction.

8. A process according to claim 1, wherein the lipophilic concentrate comprises a pharmaceutically active substance, a resin, a smell and flavor providing substance, or a volatile-in-steam component.

9. A process according to claim 8, wherein the lipophilic concentrate comprises a volatile-in-steam component, said component being an ethereal oil, a naphthoquinone derivative, or an alkaloid.

10. A process according to claim 1, wherein the organic solvent is a polar solvent.

11. A process according to claim 10, wherein the polar solvent is an alcohol, a ketone or an ester.

12. A process according to claim 1, wherein the dried organic phase contains not more than 2% by weight water.

13. A process according to claim 12, wherein the dried organic phase is essentially free of water.

14. A process according to claim 1, wherein the drying agent is a vegetable- or animal- or chemical-water-absorbing material.

15. A process according to claim 14, wherein the drying agent is tragacanth, gelatin, a water-free sodium sulfate, a water-free magnesium sulfate, a water-free calcium chloride, a molecular sieve, or a combination thereof.

16. A process according to claim 1, wherein distillation is under vacuum at a temperature of up to 60° C.

17. A process for preparing a complete extract of medical plants and/or spice plants, or parts thereof, comprising the hydrophilic components thereof and both volatile-in-steam lipophilic components and non-volatile-in-steam lipophilic components thereof, said process comprising obtaining a lipophilic concentrate according to the process of claim 12, mixing the resulting vegetable solid matter residue with water or a water miscible diluted organic solvent and extracting to form a solid matter/liquid phase extraction mixture; separating the solid matter from the liquid phase; distilling the liquid phase to form a hydrophilic component concentrate; and mixing the hydrophilic and lipophilic concentrates to form a complete extract.

* * * * *

UNITED STATES PATENT AND TRADEMARK OFFICE
CERTIFICATE OF CORRECTION

PATENT NO. : 5,176,913
DATED : January 5, 1993
INVENTOR(S) : Hans HONERLAGEN et al.

It is certified that error appears in the above-indentified patent and that said Letters Patent is hereby corrected as shown below:

Column 10,

Claim 17, line 7, change "12" to --1--.

Signed and Sealed this

Eighteenth Day of January, 1994

Attest:

BRUCE LEHMAN

Attesting Officer     Commissioner of Patents and Trademarks